(12) United States Patent
Kiridena et al.

(10) Patent No.: US 10,202,497 B2
(45) Date of Patent: Feb. 12, 2019

(54) MICROWAVE EXTRACTION TECHNIQUE FOR RUBBER AND RESIN ANALYSIS

(71) Applicant: BRIDGESTONE CORPORATION, Tokyo (JP)

(72) Inventors: Waruna C. B. Kiridena, Copley, OH (US); Yingyi Huang, Hudson, OH (US)

(73) Assignee: Bridgestone Corporation, Tokyo (JP)

( * ) Notice: Subject to any disclaimer, the term of this patent is extended or adjusted under 35 U.S.C. 154(b) by 94 days.

(21) Appl. No.: 15/260,843

(22) Filed: Sep. 9, 2016

(65) Prior Publication Data

US 2017/0073479 A1 Mar. 16, 2017

Related U.S. Application Data

(60) Provisional application No. 62/216,838, filed on Sep. 10, 2015.

(51) Int. Cl.
C08J 3/28 (2006.01)
G01N 33/44 (2006.01)

(52) U.S. Cl.
CPC ............. *C08J 3/28* (2013.01); *G01N 33/442* (2013.01); *G01N 33/445* (2013.01); *C08J 2307/00* (2013.01)

(58) Field of Classification Search
CPC ....... C08J 3/28; C08J 2307/00; G01N 33/442; G01N 33/445
See application file for complete search history.

(56) References Cited

U.S. PATENT DOCUMENTS

| | | | |
|---|---|---|---|
| 3,372,076 A | 3/1968 | Wilkinson | |
| 4,118,282 A * | 10/1978 | Wallace | C10B 19/00 201/2.5 |
| 4,405,532 A * | 9/1983 | Gutierrez | A01N 3/00 422/40 |
| 4,435,337 A * | 3/1984 | Kay | C08J 11/06 528/491 |
| 4,526,959 A * | 7/1985 | Kay | C08J 11/06 526/348 |
| 4,530,995 A * | 7/1985 | Gutierrez | A01N 3/00 524/255 |
| 4,591,631 A * | 5/1986 | Beattie | C09F 1/00 528/493 |
| 4,623,713 A * | 11/1986 | Beinor | C08C 2/00 526/335 |
| 4,681,929 A * | 7/1987 | Cole | C09F 1/00 528/493 |
| 4,880,135 A | 11/1989 | Neou | |
| 6,054,525 A * | 4/2000 | Schloman, Jr. | C08L 7/02 524/575.5 |
| 6,287,526 B1 * | 9/2001 | Hargett, Jr. | B01J 19/0073 204/157.15 |
| 6,288,379 B1 * | 9/2001 | Greene | B01J 19/126 219/679 |
| 6,373,040 B2 * | 4/2002 | Thomas | B01J 19/126 219/679 |
| 8,815,965 B2 * | 8/2014 | Cole | C08C 1/02 521/44.5 |
| 9,474,283 B2 * | 10/2016 | Silberstein | A61K 8/63 |
| 9,637,562 B2 * | 5/2017 | Huang | C08C 1/04 |
| 9,890,262 B2 * | 2/2018 | Huang | C08C 1/04 |
| 2007/0004812 A1 * | 1/2007 | Karthauser | B01D 11/0203 521/40 |
| 2009/0099327 A1 * | 4/2009 | Cornish | B01D 11/0203 528/1 |
| 2011/0303524 A1 * | 12/2011 | Lee | B01D 1/0029 201/2 |
| 2013/0295204 A1 * | 11/2013 | Silberstein | A61K 8/63 424/725 |
| 2014/0123973 A1 | 5/2014 | Pangaea | |
| 2014/0213696 A1 | 7/2014 | Martin et al. | |
| 2014/0308372 A1 * | 10/2014 | Soudant | A61Q 17/00 424/725 |
| 2014/0309414 A1 * | 10/2014 | Zhang | C08B 37/0003 536/123.1 |

(Continued)

FOREIGN PATENT DOCUMENTS

| | | |
|---|---|---|
| CN | 1295805 A | 5/2001 |
| CN | 103691147 A | 4/2014 |

(Continued)

OTHER PUBLICATIONS

Bhat et al., "Microwave method for rapid extraction of rubber and resin from plant tissue", 1989.*
Parerea et al., "Microwave-assisted extraction versus Soxhlet extraction for the analysis of short-chain chlorinated alkanes in sediments", 2004.*
McGinnies et al., Guayule:A Rubber-Producing Shrub for Aird and Smiarid Regions, 1975 (pp. 1-25).*
"Microwave-Assisted Extraction Using U.S. EPA Method 3546", CEM Corporation, Feb. 2002.*
Mandal, et. al.; Microwave Assisted Extraction—An Innovative and Promising Extraction Tool for Medicinal Plant Research; Jan.-May 2007, Pharmacognosy Reviews vol. 1, Issue 1, http://www.phcogrev.com.

*Primary Examiner* — David A Rogers
(74) *Attorney, Agent, or Firm* — Meredith E. Hooker; J. Gregory Chrisman

(57) ABSTRACT

Methods are described for microwave extraction of a component from a rubber-containing plant by providing a container holding a mixture of a sample of the rubber-containing plant and a solvent, placing the container holding the mixture in a vessel, irradiating the mixture in the vessel to increase the temperature of the mixture to extract the component from the sample of the rubber-containing plant into the solvent, and separating the extracted component from the solvent to quantify the amount of the component in the sample. Methods are also described for quantifying the amount of natural rubber in a sample from a rubber-containing plant and quantifying the amount of resin in a sample from a rubber-containing plant.

20 Claims, No Drawings

(56) References Cited

U.S. PATENT DOCUMENTS

| | | | | |
|---|---|---|---|---|
| 2015/0232583 A1* | 8/2015 | Fraley | ............ | C08C 1/02 |
| | | | | 526/335 |
| 2016/0159956 A1* | 6/2016 | Thiele | ............ | C08F 36/06 |
| | | | | 524/526 |
| 2016/0297954 A1* | 10/2016 | Sakaki | ............ | B60C 1/00 |
| 2017/0073479 A1 | 3/2017 | Kiridena et al. | | |

FOREIGN PATENT DOCUMENTS

| | | | | |
|---|---|---|---|---|
| CN | 103897806 A | | 7/2014 | |
| CN | 104083896 A | | 10/2014 | |
| CN | 104628731 B | * | 2/2017 | |
| FR | 3003181 | | 9/2014 | |
| JP | 2007245095 A | * | 9/2007 | |
| JP | 2007289916 A | * | 11/2007 | |
| JP | 2008073605 A | * | 4/2008 | |
| WO | WO 2013134430 A1 | * | 9/2013 | ......... C08C 1/04 |

* cited by examiner

MICROWAVE EXTRACTION TECHNIQUE FOR RUBBER AND RESIN ANALYSIS

This application claims the benefit of U.S. provisional application Ser. No. 62/216,838 filed Sep. 10, 2015, the contents of which are incorporated herein in their entirety by reference.

TECHNICAL FIELD

The present disclosure relates to a method for microwave extraction of a component from a rubber-containing plant. The present disclosure also relates to microwave extraction methods for quantifying an amount of natural rubber, resin, or a combination thereof, in a rubber-containing plant from testing a sample of the plant.

BACKGROUND

Certain plants represent sustainable sources of natural rubber. Natural rubber can be extracted from such plants for industry use, for example, in the tire, medical, and consumer products industries. One plant, guayule, is a perennial shrub that is a renewable source of natural rubber. The natural rubber extracted from guayule, which is native to Southwestern U.S., can replace petroleum-based synthetics and reduce reliance on imported natural rubber. The guayule is desirable because it advantageously requires relatively low amounts of water and pesticides, which reduces the costs of raising and harvesting this sustainable source of natural rubber. Another plant, the *hevea* tree, is also a renewable source of natural rubber. The *hevea* tree represents the primary source of natural rubber used in tire production.

Breeding and harvesting methods for rubber-bearing plants focus on maximizing the amount of available extractable rubber. Rapid screening methods for estimating the amount of natural rubber in harvestable plants has proven difficult. For example, guayule, which has rubber throughout its plant tissues, often requires time intensive methods and lengthy sample preparation for estimating extractable rubber content. Extensive sample preparation and long analysis times can substantially limit the number of analyses which can be completed each day.

Currently available Soxhlet extraction methods are low throughput methods that require large amounts of solvent and extensive laboratory preparation. Analysis time using a Soxhlet extraction method is lengthy and thus such use is not suitable for rapid screening of plants. There remains a need for rapid, high throughput, methods for accurately quantifying the amount of natural rubber in plants.

SUMMARY

Provided herein is a method for microwave extraction of a component from a rubber-containing plant. The method includes providing a container for holding a mixture of a sample of the rubber-containing plant and a solvent. The container holding the mixture is placed in a vessel and the mixture is irradiated to increase the temperature of the mixture to facilitate the extraction of the component from the sample of the rubber-containing plant into the solvent. The extracted component is separated from the solvent to quantify the amount of the component in the sample.

In one or more embodiments, the rubber-containing plant is *Parthenium* argentatum (a Guayule plant), *Hevea brasilensis, Taraxacum officinale* (dandelion), *Taraxacum Kok-Saghyz* (Russian dandelion), *Euphorbia lathyris* (gopher plant), *Parthenium incanum* (mariola), *Chrysothamnus nauseosus* (rabbitbrush), *Pedilanthus macrocarpus* (candililla), *Asclepias syriaca, speciosa, subulata, incarnata,* et at (milkweeds), *Solidago altissima, graminifolia, rigida, leavenworthii,* et al (goldenrods), *Cacalia atripilicifolia* (pale Indian plantain), *Pycnanthemum incanum* (mountain mint), *Teucreum canadense* (American germander), *Campanula Americana* (tall bellflower), *Lactuaca serriola* (prickly lettuce), *Ficus bengalensis, carica, elastica,* et al (a *ficus* plant), *Castilla elastic* (a Panama rubber tree), *Cryptostegia grandiflora* (rubbervine), *Sonchus arvensis, oleraceous,* et at (sow thistle), *Silphium* (a rosin weed), or a combination thereof.

In one or more embodiments, the sample of the rubber-containing plant comprises roots, bark, stem material, branch material, leaf material or a combination thereof. In one or more embodiments, the method is non-destructive to the rubber-containing plant. In one or more embodiments, the component being extracted from the sample is selected from the group consisting of natural rubber, resin, or a combination thereof.

In one or more embodiments, a method for microwave extraction of a component from a rubber-containing plant further includes extracting two components from the sample of a rubber-containing plant during the irradiating step. Optionally, this method can further include separating the two components from the solvent or two solvents and quantifying the amount of the two extracted components in the sample.

In one or more embodiments, a method for microwave extraction of a component from a rubber-containing plant sample can further include maintaining the mixture during irradiation at a temperature in the range of 80° to 110° C. for a period of 20 to 60 minutes to extract the component from the sample of the rubber-containing plant. Optionally, this method can further include increasing the temperature of the mixture in the container at a rate of at least 5° C. per minute until the mixture is at least 80° C. Optionally, this method can also include maintaining the mixture in during irradiation at a temperature in the range of 80° to 110° C. for less than 45 minutes.

In one or more embodiments, the vessel is a microwave. Optionally, the microwave is equipped with temperature probes, for example a plurality of probes, for monitoring the temperature of the mixture in each container during cheating by irradiation. Optionally, this method can further include placing 2 to 50 containers, each containing a mixture of a sample of a rubber-containing plant and a solvent, in the microwave to extract a component from the samples of a rubber-containing plant. In one or more embodiments, the mixture contains two solvents. In one or more embodiments, the mixture has a total solvent to sample of rubber-containing plant ratio of 2:1 to 6:1. In one or more embodiments, the mixture has not more than 50 mL of solvent. In some embodiments, the mixture has not more than 15 g of sample of rubber-containing plant.

In one or more embodiment, a method is provided for quantifying the amount of natural rubber in a sample from a rubber-containing plant and further using that quantification to determine the amount of natural rubber is the rubber-containing plant used to prepare the sample. This method can include placing a closed container holding a mixture of the sample from the rubber-containing plant and a solvent in a microwave vessel. The mixture is irradiated to increase the temperature of the mixture in the container to a range of 80° to 100° C. for a period of 20 to 60 minutes to facilitate the extraction of natural rubber from the sample into the solvent. The amount of natural rubber present in the sample is quantified by separating from the solvent and weighing the extracted natural rubber. In one or more embodiments, the mixture has a total solvent to sample of rubber-containing plant ratio of 2:1 to 6:1.

In another embodiment, a method is provided for quantifying the amount of resin in a sample from a rubber-containing plant. This method includes placing a closed container holding a mixture of the sample from the rubber-containing plant and a solvent in a microwave vessel. The mixture is irradiated to increase the temperature of the mixture in the container to a range of 80° to 100° C. for a period of 20 to 60 minutes to facilitate the extraction of the resin from the sample into the solvent. The amount of resin present in the sample is quantified by separating from the solvent and weighing the extracted resin. In one or more embodiments, the mixture of this method has a total solvent to sample of rubber-containing plant ratio of 2:1 to 6:1.

DETAILED DESCRIPTION

Herein, when a range such as 20-60 (or 20 to 60) is given, this means preferably at least or more than 20 and, separately and independently, preferably not more than or less than 60. In an example, such a range defines independently at least 20, and separately and independently, not more than 60.

Provided in this disclosure are methods that may be used as a screening tool or method to determine the quantity of natural rubber and/or resin in a plant, for example, to aid in the selection of plants for harvesting or breeding. In one or more embodiments, disclosed are microwave extraction methods for quantifying or estimating an amount of natural rubber, resin, or a combination thereof, in a plant, such as a guayule, from testing a plant sample. The methods may also be used to predict the amount of extractable natural rubber or resin in a rubber-containing plant. The microwave extraction method can extract both rubber and resin from a plant sample, and each of the rubber and resin in the plant sample are separately quantified. As described below, quantifying the amount of natural rubber, resin, or a combination of both allows a user to quickly determine the presence and variant amounts of natural rubber or resin in a sampled plant, which can be further indicative of the rubber and resin contents of a batch of plants or an entire harvestable quantity of plants.

As used herein, the term "natural rubber" or "NR" means naturally occurring rubber such as can be harvested from sources such as *Hevea* rubber trees, and non-*Hevea* source (e.g., guayule shrubs, and dandelions (e.g., TKS)). The term "natural rubber" should not be construed as including synthetic forms of rubber, for example, styrene-butadiene rubbers.

As used herein, the term "resin" refers to all other non-natural rubber extractables from a plant sample. The resin can be a complex mixture of sesquiterpene ethers, triterpenoids, sugars, polysaccharides, parthenoids, glycerides of fatty acids, esters, and hard wax, wherein the make-up of the resin can vary depending on the plant sample type, cultivation site, harvest date and processing conditions.

As used herein, "plant" refers to a natural rubber- or resin-bearing plant. The plant can be a living, non-harvested plant from which a sample can be taken for extraction of rubber, resin, or both rubber and resin. The sample can be tested to determine the amount of rubber, resin, or both in the sample. The sample may be harvested from a pollarded plant, where the root system is left in the soil to generate another plant. In another example, the plant can be harvested and/or non-living, and a sample of the plant can be prepared for extraction.

Examples of such plants include, but are not limited to, a guayule shrub (*Parthenium* argentatum), a *hevea* tree (*Hevea brasilensis*), a dandelion (including but not limited to *Taraxacum officinale* and a Russian dandelion *Taraxacum Kok-Saghyz*), a gopher plant (*Euphorbia lathyris*), a mariola (*Parthenium incanum*), a rabbitbrush (*Chrysothamnus nauseosus*), a candililla (*Pedilanthus macrocarpus*), a milkweed (including but not limited to milkweed plants such as *Asclepias syriaca, speciose, incarnata*, and *subulata*, et al), a goldenrod plant (including but not limited to *Solidago altissima, graminifolia, leavenworthii*, and *rigida*), a pale Indian plaintain (*Cacalia atripilicifolia*), mountain mint (*Pycnanthemum incanum*), an American germander (*Teucreum canadense*), a tall bellflower (*Campanula Americana*), prickly lettuce (*Lactuaca serriol*), a *Ficus* plant (including but not limited to *Ficus carica, elastica*, and *benghalensis*), a Panama rubber tree (*Castilla elastica*), a rubbervine (*Cryptostegia grandiflora*), a sow thistle (*Sonchus arvensis, oleraceous*, et al), a rosin weed (*Silphium*), a combination thereof, or another plant which produces rubber and/or rubber-like hydrocarbons. Plant features that can be used for test samples include but are not limited to, stem material, leaf material, bark material, branch material, root material, or a combination thereof.

A plant sample can be prepared by harvesting, for example, by trimming a piece of a grown shrub above the ground or cutting a piece of a root below the ground. Alternatively, an entire plant can be harvested for testing. Harvested plants may be prepared in the field and/or baled for transport to a testing facility. At a testing facility, the plant material is crushed in preparation for extraction to increase the surface area of the plant sample. In some embodiments, a plant sample is crushed by milling. Any suitable milling means to prepare a plant sample for a microwave extraction method contained herein may be used including dry milling, wet milling, or in a homogenizer type mill. A plant sample may be milled using a hammer mill, roll mill, stone mill, ball mill, or pulp mill.

The methods described herein can be non-destructive to the plant being tested. The term "non-destructive" refers to a method for obtaining a sample from a plant for extracting an amount of natural rubber, resin, or both and optionally quantifying the amount of natural rubber, resin, or both natural rubber and resin in the plant, and obtaining the sample does not cause significant harm to the plant or independently cause the plant to die. The non-destructive methods for quantifying an amount of natural rubber or resin in a plant can be used for selective breeding or harvesting purposes that can increase or maximize the amount of extractable rubber that can be obtained from the plants. The methods described herein can also be used to quantify or predict the amount of natural rubber or resin in a non-living or harvested plant. For instance, quantifying the amount of natural rubber in harvested plants can predict or estimate the total amount of extractable rubber that a particular crop harvest can yield.

At least one solvent is used in the methods and examples described herein. In some embodiments, two solvents are combined as co-solvents to form a solvent mixture. The solvent or solvents are combined with the prepared plant sample material to form a mixture for extraction of components from the plant material. In some embodiments, at least one solvent is a polar solvent or a dipolar solvent. In one embodiment, the polar or dipolar solvent can be anhydrous.

More specifically, the total solvent system, polar or dipolar solvent can include less than about 0.5 weight percent (wt %) water, less than about 0.2 wt % water, less than 0.1 wt % water, or less than 0.05 wt % water. In other embodiments, the total solvent system, polar or dipolar solvent can have moisture content in the range of 0.5 to 20 wt %, 1 to 15 wt % or 3 to 10 wt %.

In addition, it is preferred that the polar or dipolar solvent (or mixture of polar or dipolar solvents) constitute a portion of the solvent system; for example, in one embodiment the polar or dipolar solvent(s) constitute(s) 10 to 35 weight percent (wt %) and preferably 15 to 25 wt % of the total solvent system.

Examples of organic polar solvents include the ketones having from 3 to 8 carbon atoms such as methyl ethyl ketone, acetone and the like. Acetone is a highly preferred solvent. Other organic polar solvents include the esters having from 3 to 8 carbon atoms, such as the formates, acetates, propionates, and the like. Another polar solvent is the ethers having from 2 to 8 carbon atoms, such as dimethyl ether, diethyl ether and the like as well as cyclic ethers of from 4 to 8 carbon atoms such as tetrahydrofuran, and the like. Moreover alcohols, having from 1 to 8 carbon atoms such as methanol and ethanol can also be utilized.

Dipolar solvents can include, but are not limited to, dimethyl formamide, diethyl formamide, dimethyl acetamide, diethyl acetamide, N-methyl-2-pyrrolidone, N-ethyl-2-pyrrolidone, hexamethyl phosphorotriamide, dimethyl sulfoxide, acetonitrile, benzonitrile, nitromethane, nitroethane, nitrobenzene, sulfolane and their mixtures.

In a co-solvent system, a non-polar solvent can be used in addition to a polar solvent. The hydrocarbon solvents, or non-polar solvents, include the alkanes having from 4 to 9 carbon atoms such as pentane, hexane, heptane, and the like, with pentane and hexane being preferred. Cycloalkanes and alkyl cycloalkanes having from 5 to 10 carbon atoms such as cyclohexane can also be utilized. Other hydrocarbon solvents are various aromatics and alkyl substituted aromatics having from 6 to 12 carbon atoms such as benzene, toluene, xylene, and the like.

The non-polar solvent can constitute at least about 25 wt % of the solvent system. For example, in some embodiments it is preferred that the non-polar solvent(s) constitute(s) at least about 50 wt % of the solvent system. In some embodiments, it is preferred that the non-polar solvent(s) constitute(s) at least about 75 wt % of the solvent system. In a further embodiment, the non-polar solvent(s) constitute(s) at least about 90 wt % of the solvent system.

In some embodiments, the solvent mixture includes an alkane and an alcohol. The solvent mixture can include a greater percentage of alkane than alcohol. The solvent mixture can be 80:20 alkane:alcohol respectively. An alkane can be a hexane, a pentane, a cyclohexane, a mixture thereof, or any alkane sufficient for a microwave extraction method contained herein. Additionally, an ether could be substituted for the alkane, such as ethyl ether, or a benzene, a toluene, or a chlorinated solvent. An alcohol can be acetone, methanol, ethanol, a mixture thereof, or any alcohol sufficient for a microwave extraction method contained herein.

A plant sample for use in the microwave extraction methods can be any desirable size, for example, the sample of the plant can have a weight in the range of 2 to 20 grams (g), or 4 to 15 g, or less than 20, 15, 12 or 10 g. The plant sample can be dried such that the water content is below 1 weight percent or in the range of 0.1 to 1 weight percent. In other embodiments, the plant sample can have a moisture content in the range of 1 to 30, 2 to 20 or 3 to 10 weight percent, which moisture content can be present before the plant sample is combined with the solvent.

The amount of solvent or solvent mixture (e.g., a co-solvent mixture) used with a sample for use in a microwave extraction method can be in the range of 10 to 50 ml, 10 to 30 ml or about 20, 25 or 30 ml.

The plant sample and solvent mixture is preferably such that the solvent entirely submerges the plant material when the mixture is held in the container. In one or more embodiments, the mixture in the container can have a ratio of total solvent to sample of rubber-containing plant in the range of 2:1 to 6:1 or about 3:1, 3.5:1, 4:1, 4.5:1, 5:1 or 5.5:1. In an example mixture, a plant sample can be in the range of 5 to 10 g and a total solvent content can be in the range of 20 to 35 ml.

In one or more embodiments, the plant sample and solvent mixture can be anhydrous. For example, the mixture can include less than about 0.5 wt % water, less than about 0.2 wt % water, or less than 0.1 wt % water, and in some embodiments, less than 0.05 wt % water. The mixture can also have a water content, either provided by the solvent system, plant sample or a combination of both. In one ore embodiments, the mixture can have a water content in the range of 1 to 30 wt %, 2 to 20 wt % or 3 to 10 wt %.

Vessels for heating and facilitating the extraction of natural rubber and resin are used in the methods and examples described herein. As used herein, the term "microwave vessel," or "microwave" refers to any receptacle or apparatus capable of receiving and/or producing microwaves. A suitable vessel may be a microwave apparatus. In some embodiments, a vessel may be capable of use for an open-container microwave extraction method or a closed-container microwave extraction method, wherein the container holding the mixture is either open or closed during irradiation. In some embodiments, a container is placed on a turntable within the vessel so that the container rotates or otherwise changes position during irradiation. One example of a microwave system that can be used for extraction of natural rubber and resin from a plant sample is a MARS 5 Microwave System.

In one or more embodiments, a microwave vessel can be operated at atmospheric pressure such that the pressure in the container and/or interior chamber of the microwave is maintained at or near standard atmospheric pressure. In one or more embodiments, the container can be closed (e.g., with a lid or screw cap) during irradiating such that the pressure in the container is increased as the temperature of the mixture increases. In one or more embodiments, a vessel can be equipped with at least one pressure sensor or a plurality of pressure sensors, for example, a pressure sensor that can interact with a container in the vessel and measure the pressure within the container. In some embodiments, the pressure within the vessel is alterable or can be maintained at a constant pressure. For example, the pressure sensor can be used to control or adjust the power input to the vessel to reduce irradiation of the mixture(s) and reduce or maintain a desirable temperature. By maintaining or controlling the temperature in the closed container, the internal pressure can be controlled.

In one or more embodiments, the pressure within a container can be in the range of 12 to 20 PSI (pounds per square inch). Containers can be equipped with a safety pressure valve or relief valve to prevent the pressure in the container from exceeding a maximum pressure, for example 20 psi.

In another embodiment, a vessel can be used that is equipped with at least one temperature sensor or a plurality of temperature sensors, for example, a temperature sensor can be arranged to measure the temperature in a container in the vessel during irradiation. A temperature sensor may be an infrared (IR) temperature sensor.

In embodiments, rubber, resin, or both rubber and resin are extracted from at least one plant sample or a plurality of plant samples. A plurality of plant samples can be in the range of 2 to 40 plant samples or more. The rubber, resin, or both rubber and resin can be extracted from the plurality of samples simultaneously during a microwave irradiation of multiple containers each holding a mixture, wherein each mixture can be unique to a specific plant material from different plants.

To extract the rubber and resin, the plant sample and solvent mixture are placed in a container or plurality of containers and the containers are arranged in a vessel for irradiating the mixture. A container can include Teflon®, glass, or any material suitable for a temperature low enough to minimize degradation of rubber in a sample and high enough to encourage extraction. In some embodiments, a container can withstand a temperature range of 80° to 110° C. A container not otherwise suited for a desired temperature range can be coated, lined, or otherwise combined with another material to become suitable for use in a microwave extraction. A container can include a PFA (perfluoroalkoxy) Teflon® liner. A container can be a MARSXpress™ Teflon® container. A MARSXpress™ Teflon® container can include a Kevlar® jacket. In some embodiments, a plurality of containers are used during each microwave extraction procedure. In some embodiments, each container includes one plant sample. A container including a plant sample can be irradiated alone within a vessel or alternatively, a plurality of containers, each including a plant sample, can be irradiated together simultaneously within a vessel. In some of the methods contained herein, forty containers can be irradiated simultaneously. In some of the methods contained herein, more than forty containers can be irradiated simultaneously.

The vessel, for example a microwave, can increase the temperature of the mixture to a desired temperature in the range of 80° to 110° C., and preferably in the range of 95° to 105° C. In one example, the mixture can be maintained in the container at about 100° C. The vessel can be programmed to irradiate the mixture at room temperature and heat the mixture to the desired temperature at a pre-determined rate, for example, the mixture can be heated at a rate of 5° to 20° C. per minute or preferably in the range of 5° to 15° C. per minute. In one example, the mixture can be heated at a rate of 10° C. per minute. The vessel can use any suitable input power level to achieve the desired heating rate, for example, a microwave power can be in the range of 500 to 2000 Watts. In one example, the microwave vessel can use a power of 800 to 1,000 Watts to irradiate one or mixtures for facilitating extraction of rubber and resin from the plant sample material.

The mixture can be maintained at a select temperature as noted above for a suitable period of time to allow the rubber and resin to be extracted into the solvent system. The mixture can be held or maintained at a determined temperature for a period of 20 to 60 minutes or more, and preferably in the range of 30 to 50 minutes, or about 35, 40 or 45 minutes. After maintaining the mixture at a temperature for a period of time, the vessel can be powered off or gradually ramped down in power to allow the mixture to cool. The mixture can be forced cooled at a desired rate or allowed to cool slowly after irradiation stops. In some embodiments, the samples are allowed to cool for about ten minutes. In some embodiments, samples are cooled using a forced-refrigeration or air cooling method.

The maximum temperature during hold time of a microwave program is a temperature low enough to minimize degradation of the rubber in the sample and high enough to achieve extraction. Temperatures may be altered by adjusting the power of the microwave vessel, temperature ramping parameters, hold time duration, and cool down time. For example, power and/or temperature could be lowered in combination with a longer hold time duration.

In some embodiments, after extraction of rubber and/or resin from a plant sample, the sample is centrifuged to separate components within the sample. In some embodiments, after extraction of rubber and/or resin from a plant sample, the sample is filtered to separate components within the sample into at least two portions. At least one component of one of the at least two portions can be quantified. For example, after irradiation, the mixture will contain a solvent or solvent system containing rubber, resin or a combination of both. The remaining plant material will be undissolved and discarded after the solvent or solvent system is separated from the remaining plant material. The solvent containing the rubber, resin or a combination thereof can be analyzed to quantify each component.

The instruments used in the methods and examples described herein to quantify the amount of extracted rubber or resin are instruments that can record signals from natural rubber and resin present in plant samples. It was found that microwave extraction can be used to extract natural rubber and resin from a plant sample and the extracted sample can be used to accurately quantify the amount of natural rubber, resin, or both rubber and resin in a tested plant. In some embodiments, quantifying is performed using at least one of the following methods: gravimetric method, nuclear magnetic resonance, gel permeation chromatography, spectroscopic method, gas chromatography, high-performance liquid chromatography, an anti-oxidant assay, and acetone extraction, a combination thereof, or an additional method capable of quantifying at least one of rubber or resin in a sample extracted from a plant.

In order to demonstrate the practice of the present invention, the following examples have been prepared and tested. The examples should not, however, be viewed as limiting the scope of the invention.

EXAMPLES

Plant Material Preparation of a 5 g Sample

Guayule plant was obtained. Plant material was crushed in a blender and percent moisture was determined. Percent moisture was determined using an MX-50 from A&D Company, Ltd. 5 grams (to the nearest 0.0001 g) of crushed plant were selected for extraction.

Plant Material Preparation of an 8 g Sample

Guayule plant was obtained. Plant material was crushed and percent moisture was determined. Percent moisture was determined using an MX-50 from A&D Company, Ltd. 8 grams (to the nearest 0.0001 g) of crushed plant were selected for extraction.

Solvent Preparation

Hexane and acetone were combined to form a 80:20 mixture of hexane:acetone.

Microwave Extraction Using a 5 g Sample

A 5 g shrub sample and 20 ml of the 80:20 hexane:acetone solvent mixture were combined and placed in a MARSXpress™ Teflon® container. The container was loaded on a rack within a vessel. A balance was loaded with 80:20

Hexane/Acetone blend. The mixture sample was irradiated using a microwave program as shown below in Table 1. The microwave power was 800 Watts at 100% power. The temperature was measured with sensors and increased at 10° C./min until reaching 100° C. The mixture sample was held at 100° C. for 40 minutes. The mixture sample was then allowed to cool.

TABLE 1

Microwave Program

| Power/W | % Power | Ramp/min | Temperature/° C. | Hold time/min |
|---|---|---|---|---|
| 800 | 100 | 10 | 100 | 40 |

Microwave Extraction Using 40 Samples

Forty 5 g shrub samples were selected. Each 5 g shrub sample was combined with 20 ml of the 80:20 hexane:acetone solvent mixture sample, and each individual combination of shrub sample and solvent was placed in an individual MARSXpress™ Teflon® container. The sample containers were loaded on a rack within a vessel. The mixture samples were irradiated using a microwave program as shown in Table 2 below. The microwave power was 800 Watts at 100% power. The temperature was measured with sensors and increased at 10° C./min until reaching 100° C. The mixture samples were held at 100° C. for 40 minutes. The mixture samples were then allowed to cool.

TABLE 2

Microwave Program

| Power/W | % Power | Ramp/min | Temperature/° C. | Hold time/min |
|---|---|---|---|---|
| 800 | 100 | 10 | 100 | 40 |

Gravimetric Method for Quantification of Rubber and Resin

A gravimetric method was used to quantify the amounts of natural rubber and resin in the irradiated mixture samples containing extracted rubber and resin. A mixture sample containing microwave-extracted rubber and resin was transferred from the container to a fresh glass screw cap vial (caps with polytetrafluoroethylene (PTFE) septa) and the mixture sample was called "stock solution 1." The stock solution 1 was filtered using a disposable syringe and syringe filter (Fisherbrand™ PTFE filter 0.25 mm diameter and 0.45 micron filter size) to a 7 ml fresh screw cap vial to remove the fines. This filtered solution was called "stock solution 2." An empty 15 ml centrifuge tube and cap were weighed to the nearest 0.0001 g. 5 ml of stock solution 2 was transferred to the centrifuge tube. 10 ml of acetone was added to the stock solution 2 in the centrifuge tube to coagulate rubber present in the stock solution 2. The centrifuge tube containing the stock solution 2 plus acetone was centrifuged at 1500 rpm (revolutions per minute) for 30 minutes.

An empty aluminum weighing dish was weighed to the nearest 0.0001 g. The supernatant in the centrifuge tube was decanted into the weighing dish. 10 ml of acetone or methanol was added to the centrifuge tube to repeat the rubber coagulation step. The centrifuge tube was centrifuged at 1500 rpm for 20 minutes. The supernatant in the centrifuge tube was decanted into the same weighing dish. The weighing pan and contents were weighed to the nearest 0.0001 g.

The centrifuge tube containing the resin sample was placed in a fume hood to allow most of the remaining solvent to evaporate. The centrifuge tube and cap were then placed into a vacuum oven. The resin sample was dried under a vacuum at 60° C. for 30 to 45 minutes. The centrifuge tube cap was placed back on the tube and the tube was cooled to room temperature. The capped tube and contents were weighed to the nearest 0.0001 g.

The microwave extraction-gravimetric quantification method is a robust, reproducible, and high throughput rubber and resin analysis method for analyzing a rubber containing plant such as the Guayule plant.

Calculations

The amount of rubber and the amount of resin in a plant were calculated using the formulas below.

M=% moisture
WS=weight of shrub sample
V1=volume of fresh solvent added to microwave vessel
V2=volume of stock solution 2 transferred to centrifuge tube
T1=weight of empty dry centrifuge tube with cap
T2=weight of centrifuge tube with cap plus vacuum oven dried rubber
P1=weight of empty dry aluminum pan
P2=weight of aluminum pan plus vacuum oven dried resin $$\% \text{ Rubber} = \frac{(T2-T1)*\left(\frac{V_1}{V_2}\right)}{WS*\left(1-\frac{M}{100}\right)} \quad \% \text{ Resin} = \frac{(P2-P1)*\left(\frac{V_1}{V_2}\right)}{WS*\left(1-\frac{M}{100}\right)}$$

The plant material preparation, solvent preparation, microwave extraction method and gravimetric calculation method described directly above yield the results shown in Tables 3, 4 and 5. The results of the microwave extraction shown in Table 3 were compared to processing the same sample material with a Soxhlet Extraction.

TABLE 3

Microwave Extraction vs. Soxhlet Extraction

| Shrub Sample Type | % Rubber | | % Resin | |
|---|---|---|---|---|
| | Soxhlet | Microwave | Soxhlet | Microwave |
| Guayule Plant | 1.68 | 1.50 | 7.84 | 7.53 |
| | 1.60 | 1.50 | 8.08 | 7.38 |
| Guayule plant | 2.00 | 2.60 | 7.26 | 8.3 |
| | 1.86 | 2.60 | 7.36 | 8.5 |

TABLE 4

Microwave Extraction

| Shrub Sample (Guayule) | % Rubber | | | % Resin | | |
|---|---|---|---|---|---|---|
| Sample #1 | 1.75 | 1.77 | 1.74 | 8.78 | 8.63 | 8.61 |
| Sample #2 | 2.06 | 2.76 | 2.20 | 6.85 | 8.42 | 6.88 |
| Sample #3 | 2.48 | 2.82 | 2.35 | 7.50 | 8.12 | 6.86 |
| Sample #4 | 1.31 | 1.63 | 1.22 | 5.81 | 6.07 | 5.29 |
| Sample #5 | 0.63 | 0.63 | 0.51 | 5.63 | 5.71 | 8.33 |
| Sample #6 | 0.26 | 0.21 | 0.23 | 5.47 | 6.98 | 5.09 |

TABLE 5

| Microwave Extraction | | | |
| --- | --- | --- | --- |
| Shrub Sample (Guayule) | % Moisture | % Rubber | % Resin |
| Sample #7 | 9.69 | 0.69 | 4.02 |
| Sample #8 | 9.38 | 0.66 | 4.05 |
| Sample #9 | 8.81 | 0.65 | 4.30 |
| Sample #10 | 8.79 | 0.54 | 3.34 |
| Sample #11 | 8.73 | 0.55 | 4.42 |
| Sample #12 | 8.95 | 0.68 | 4.55 |

As understood in the art, the microwave extraction conditions and parameters can be be adjusted to accommodate plant type, sample size, solvent selection, etc. All references, including but not limited to patents, patent applications, and non-patent literature are hereby incorporated by reference herein in their entirety.

While various aspects and embodiments have been disclosed herein, other aspects and embodiments will be apparent to those skilled in the art. The various aspects and embodiments disclosed herein are for purposes of illustration and are not intended to be limiting.

What is claimed is:

1. A method for microwave extraction of a component from a non-harvested rubber-containing plant comprising the steps of:
   a. providing a container holding a mixture of a sample of the non-harvested rubber-containing plant and a solvent, the mixture comprising less than 50 mL of solvent;
   b. placing the container holding the mixture in a vessel;
   c. irradiating the mixture in the vessel to increase the temperature of the mixture to 80° C. to 110° C., maintaining the mixture at a temperature in the range of 80° C. to 110° C. for a period of 20 to 60 minutes to extract the component from the sample of the non-harvested rubber-containing plant into the solvent, the component comprising rubber and resin; and
   d. separating the extracted component from the solvent to quantify the amount of at least one of the rubber and the resin in the component in the sample,
   wherein the method being a screening method that is non-destructive and does not cause significant harm to the non-harvested rubber-containing plant, wherein the sample is prepared with a trimmed piece of the non-harvested rubber-containing plant.

2. The method of claim 1, the rubber-containing plant being *Parthenium* argentatum (a Guayule plant), *Hevea brasilensis, Taraxacum officinale* (dandelion), *Taraxacum Kok-Saghyz* (Russian dandelion), *Euphorbia lathyris* (gopher plant), *Parthenium incanum* (mariola), *Chrysothamnus nauseosus* (rabbitbrush), *Pedilanthus macrocarpus* (candililla), *Asclepias syriaca, speciosa, subulata, incarnate,* et at (milkweeds), *Solidago altissima, graminifolia, rigida, leavenworthii,* et at (goldenrods), *Cacalia atripilicifolia* (pale Indian plantain), *Pycnanthemum incanum* (mountain mint), *Teucreum canadense* (American germander), *Campanula Americana* (tall bellflower), *Lactuaca serriola* (prickly lettuce), *Ficus bengalensis, carica, elastic,* et at (a *ficus* plant), *Castilla elastic* (a Panama rubber tree), *Cryptostegia grandiflora* (rubbervine), *Sonchus arvensis, oleraceous,* et at (sow thistle), *Silphium* (a rosin weed), or a combination thereof.

3. The method of claim 1, the sample of the non-harvested rubber-containing plant comprising bark, stem material, branch material, leaf material or a combination thereof.

4. The method of claim 1, further comprising quantifying the amount of both the rubber and the resin in the sample.

5. The method of claim 1, the container being closed during irradiating such that the pressure in the container is increased.

6. The method of claim 1, increasing the temperature of the mixture in the container at a rate of 5° C. to 15° C. per minute until the mixture is at least 80° C.

7. The method of claim 1, the mixture being maintained in step c at a temperature in the range of 80° to 110° C. for less than 45 minutes.

8. The method of claim 1, the vessel being a microwave oven.

9. The method of claim 8, the microwave being equipped with temperature probes for monitoring the temperature of the mixture in the container during step c.

10. The method of claim 8, further comprising placing 2 to 50 containers each containing a mixture of a sample of the non-harvested rubber-containing plant and a solvent in the microwave to extract a component from the samples of the non-harvested rubber-containing plant.

11. The method of claim 1, the mixture consisting of two anhydrous solvents and the sample of the non-harvested rubber-containing plant.

12. The method of claim 1, the mixture having a total solvent to sample of rubber-containing plant ratio of 2:1 to 6:1.

13. The method of claim 1, the mixture having not more than 50 mL of solvent and not more than 20 g of sample of the non-harvested rubber-containing plant.

14. The method of claim 1, the mixture having not more than 15 g of sample of rubber-containing plant.

15. A method of quantifying the amount of natural rubber in a sample from a non-harvested rubber-containing plant that is non-destructive and does not cause significant harm to the non-harvested rubber-containing plant, the method comprising the steps of: a. placing a closed container holding a mixture of the sample from the non-harvested rubber-containing plant and a solvent in a microwave vessel, the mixture comprising less than 20 g of sample of non-harvested rubber-containing plant and less than 50 mL of solvent, wherein the total solvent to sample of non-harvested rubber-containing plant ratio of the mixture is 2:1 to 6:1; b. irradiating the mixture to increase the temperature of the mixture in the container at a rate of 5° to 20° C. per minute to a range of 80° to 100° C., maintaining the mixture in the container for a period of 20 to 60 minutes to extract natural rubber in the sample into the solvent; and c. quantifying the amount of natural rubber present in the sample by separating from the solvent and weighing the extracted natural rubber, wherein the method is non-destructive to the rubber-containing plant and the sample being prepared by trimming a piece from the non-harvested rubber-containing plant and wherein the non-harvested rubber-containing plant is a non-pollarded plant.

16. The method of claim 15, the solvent of the mixture consisting of one or more anhydrous solvents.

17. A method of quantifying the amount of resin in a sample from a non-harvested rubber-containing plant comprising the steps of: a. placing a closed container holding a mixture of the sample from the non-harvested rubber-containing plant and a solvent in a microwave vessel, the mixture comprising less than 20 g of sample of non-harvested rubber-containing plant and less than 50 mL of solvent, wherein the total solvent to sample of non-harvested rubber-containing plant ratio of the mixture is 2:1 to 6:1; b. irradiating the mixture to increase the temperature of the mixture in the container at a rate of 5° to 20° C. per minute to a range of 80° to 100° C., maintaining the mixture in the container for a period of 20 to 60 minutes to extract resin in the sample into the solvent; and c. quantifying the amount of resin present in the sample by separating from the solvent and weighing the extracted resin, wherein the method is non-destructive to the rubber-containing plant and the sample being prepared by trimming a piece from the non-harvested rubber-containing plant and wherein the non-harvested rubber-containing plant is a non-pollarded plant.

18. The method of claim 17, the solvent of the mixture consisting of one or more anhydrous solvents.

19. The method of claim 1, the mixture consisting of the sample of the rubber-containing plant and mixture of an alkane and a polar hydrocarbon solvent.

20. The method of claim 19, the alkane and the polar hydrocarbon solvent being anhydrous.

* * * * *